United States Patent [19]

Williams et al.

[11] Plant 4,322

[45] Oct. 24, 1978

[54] APPLE TREE (COOP 13)

[75] Inventors: Edwin B. Williams, Lafayette; Jules Janick; Frank H. Emerson, both of West Lafayette, all of Ind.; Daniel F. Dayton, Urbana, Ill.; L. Fredric Hough, Bloomsbury; Catherine Bailey, Englishtown, both of N.J.

[73] Assignee: Purdue Research Foundation, West Lafayette, Ind.

[21] Appl. No.: 821,644

[22] Filed: Aug. 4, 1977

[51] Int. Cl.[2] ..... A01H 5/03

[52] U.S. Cl. ..... Plt./34

[58] Field of Search ..... Plt./34

*Primary Examiner*—Robert E. Bagwill

*Attorney, Agent, or Firm*—John R. Nesbitt

[57] ABSTRACT

This invention relates to a new cultivar of an apple tree which is scab resistant, and is characterized by a maturity 7 weeks before Delicious and 3½ weeks before Prima.

1 Drawing Figure

1

This invention is a new and distinct cultivar of apple tree. It was discovered by applicants in August, 1971, at Lafayette, Ind., in the course of an attempt to develop improved apple trees with high fruit quality and resistance to *Venturia inaequalis* (Cke.) Wint., the casual agent for the apple scab disease. The tree is a seedling of known parentage planted in 1966 in Block C of the Hinsley Breeding Orchard at the Horticultural Farm of the Purdue University Agricultural Experiment Station, Lafayette, Ind. In the above orchard, its position was Row 21, Tree 200, having the description PRI 2175-7 in our breeding records.

The present new cultivar, which is designated as Coop 13, is a seedling produced from crossing 'Raritan' as the seed parent and the seedling PRI 1018-101 as the pollen parent in 1965 at New Brunswick, N.J. This new cultivar carries a genetic factor, $V_f$, inherited from *Malus floribunda* 821 which causes it to be resistant to infection caused by *Venturia inaequalis*. The presence of this genetic factor has been repeatedly proven by controlled inoculation tests in the Purdue greenhouse of the seedling and of its offspring produced from controlled crosses. The complete pedigree is shown below:

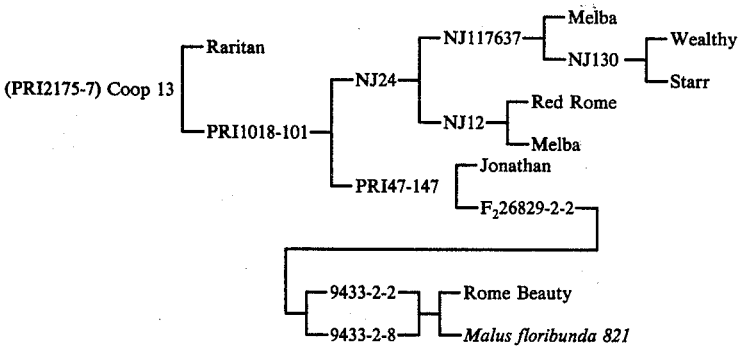

The new cultivar produces a vigorous tree with good annual crops. It is resistant to scab and moderately resistant to fireblight and powdery mildew.

The tree flowers just prior to 'McIntosh' and 'Priscilla' which is described in U.S. Plant Pat. No. 3,488. The apple fruit has good quality. Fruit hold texture and quality 2 months or more at 34° F.

After observation, the selection was asexually propagated by grafting on seedling apple roots. The grafted

2 material has maintained the desired characteristics after propagation.

The accompanying drawing (color photograph) shows a typical example of fruit and foliage of Coop 13. The following is a detailed description of the new cultivar with the color description according to the Horticultural Colour Chart issued by the British Colour Counsel in collaboration with the Royal Horticultural Society.

FLOWER

Pedicel: 3 cm (1¼ inches) in length.

Corolla: 4 cm (1⅝ inches) in diameter at anthesis.

Color: Magenta from Plate 27/1 (bud) to 27/3 (open flowers).

FRUIT

Shape: Oblate, regular.

Size: Axial diameter 7.5 (3 inches), transverse diameter 6.8 cm (2¾ inches).

Color: Undercolor aureolin (Plant 3/2), overcolor 90% chrysanthemum crimson (Plate 824), faint stripes on light side.

Skin: Smooth, waxy with inconspicuous white dots, medium thick but not tough, no russeting.

Stem: 2.2 cm (⅞ inch), medium thickness.

Cavity: Acuminate, deep, medium width, smooth.

Basin: Medium depth and broad.

Calyx: Persistent, curved to upright, closed.

Calyx tube: Urn-shaped.

Stamens: Marginal.

Core line: Clasping.
Core: Distant, closed, medium.
Carpels: Roundish, truncate, smooth.
Seed: Acute, not tufted.
Flesh:
*Texture.*—Medium, coarse, firm, breaking.
*Quality.*—Good, mild subacid.
*Color.*—Aureolin (Plate 3/1).
Maturity season: 7 weeks before "Delicious".
Keeping quality: Retains quality and texture 2 months or more at 34° F.
Use: Summer dessert apple.

TREE

Tree: Upright and vigorous.
Leaves: Ovate, serrate to double serrate margin apex acute, base rounded, length to width ratio = 1.6.

In particular, our new cultivar apple is distinguished by its resistance to scab and by its dessert quality and appearance as a summer apple.

We claim:

1. A new and distinct apple tree substantially as shown and described particularly characterized by resistance to apple scab, good fresh fruit quality, smooth waxy skin, ability to maintain quality in storage, and maturity approximately 7 weeks before "Delicious" and 3½ weeks before "Prima".

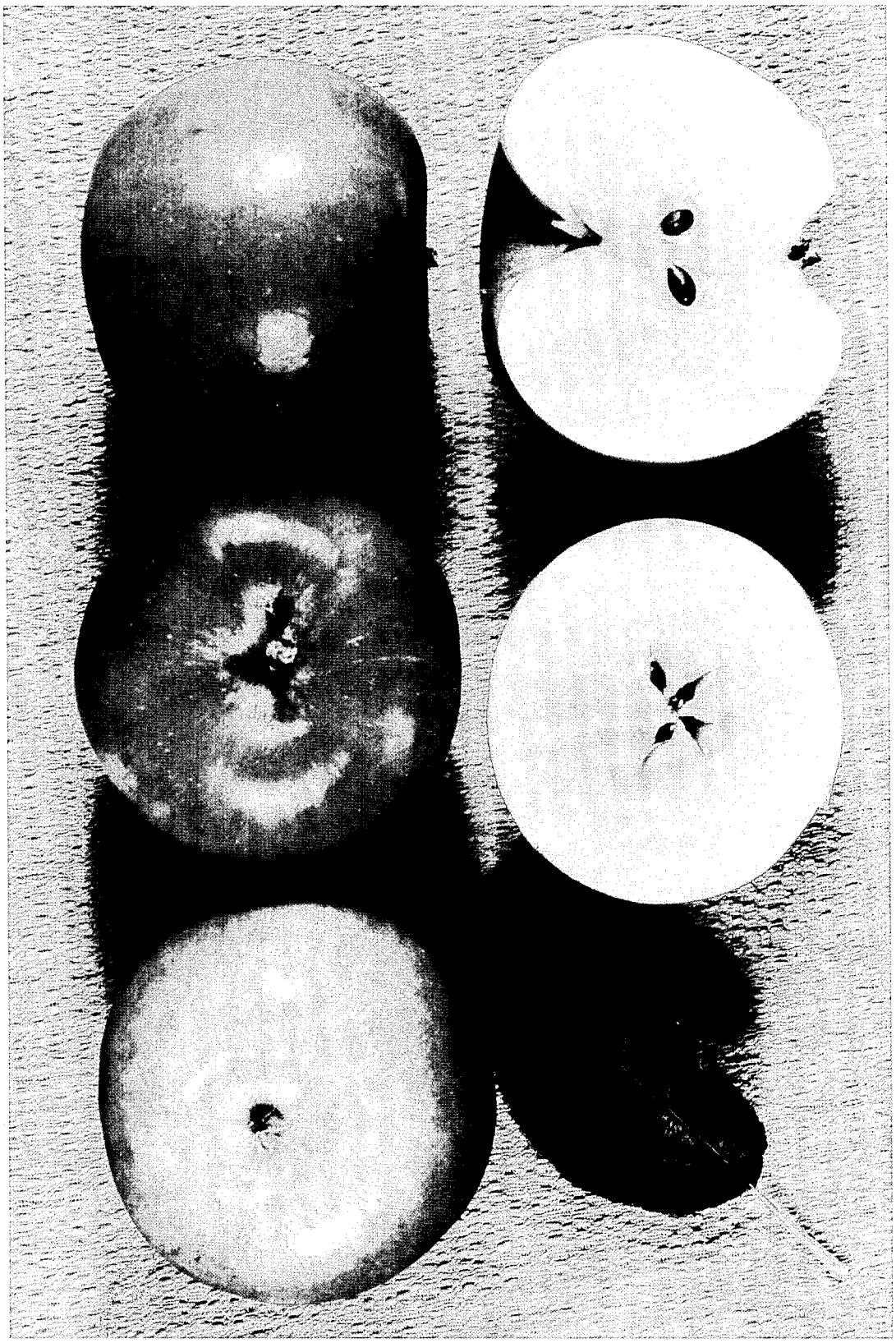

* * * * *